United States Patent [19]
Larsson

[11] Patent Number: 6,139,521
[45] Date of Patent: *Oct. 31, 2000

[54] BREASTPUMP HAVING PARTICULAR APPLICATION AS A SMALL MOTORIZED PUMP CAPABLE OF DOUBLE-BREAST PUMPING

[75] Inventor: Karl O. A. H. Larsson, Baar, Switzerland

[73] Assignee: Medela Holding AG, Baar, Switzerland

[ * ] Notice: This patent is subject to a terminal disclaimer.

[21] Appl. No.: 08/867,437

[22] Filed: Jun. 2, 1997

Related U.S. Application Data

[60] Provisional application No. 60/019,085, Jun. 3, 1996.

[51] Int. Cl.$^7$ .............................. A61M 1/06; A61M 1/00
[52] U.S. Cl. ............................................ 604/74; 604/315
[58] Field of Search .................................. 604/73–76, 94, 604/313, 315; 119/14.07, 14.05, 14.29, 14.42, 14.51

[56] References Cited

U.S. PATENT DOCUMENTS

| | | |
|---|---|---|
| 823,316 | 6/1906 | Anderson .............................. 119/14.07 |
| 1,184,293 | 5/1916 | Zeratsky . |
| 1,259,309 | 3/1918 | Somers . |
| 1,596,520 | 8/1926 | Eskholme et al. . |
| 3,238,937 | 3/1966 | Stein . |
| 3,382,867 | 5/1968 | Reaves . |
| 3,931,795 | 1/1976 | Duncan . |
| 3,990,816 | 11/1976 | Kohler et al. . |
| 4,263,912 | 4/1981 | Adams . |
| 4,486,157 | 12/1984 | Hayashi . |
| 4,607,596 | 8/1986 | Whittlestone et al. .............. 119/14.02 |
| 4,673,388 | 6/1987 | Schlensog et al. . |
| 4,857,051 | 8/1989 | Larsson . |
| 4,929,229 | 5/1990 | Larsson ..................................... 604/74 |
| 4,941,433 | 7/1990 | Hanauer . |
| 4,964,851 | 10/1990 | Larsson ..................................... 604/74 |
| 5,007,899 | 4/1991 | Larsson ..................................... 604/74 |
| 5,076,769 | 12/1991 | Shao . |
| 5,178,095 | 1/1993 | Mein . |
| 5,218,924 | 6/1993 | Thompson et al. . |
| 5,295,957 | 3/1994 | Aida et al. . |
| 5,304,129 | 4/1994 | Forgach . |
| 5,514,166 | 5/1996 | Silver et al. . |
| 5,571,084 | 11/1996 | Palmer ..................................... 604/74 |
| 5,586,518 | 12/1996 | Carrano ............................... 119/14.51 |
| 5,601,531 | 2/1997 | Silver ....................................... 604/74 |
| 5,616,125 | 4/1997 | Jelks ......................................... 604/74 |
| 5,720,722 | 2/1998 | Lockridge ................................ 604/74 |
| 5,776,098 | 7/1998 | Silver et al. ............................. 604/74 |

FOREIGN PATENT DOCUMENTS

| | | |
|---|---|---|
| 0 123 269 | 4/1984 | European Pat. Off. . |
| 0 733 376 A2 | 9/1996 | European Pat. Off. . |
| 33 28 725 A1 | 2/1984 | Germany . |
| 158 976 | 5/1957 | Sweden . |
| 0762701 | 12/1956 | United Kingdom . |
| 2 082 920 | 3/1982 | United Kingdom . |
| 2 127 293 | 4/1984 | United Kingdom . |

OTHER PUBLICATIONS

The Whittlestone Breastmilker, Model Havenwood MK III Operating Manual, 1978.
Circle Caring Brochure, Ameda Egnell, 1991.
Medela Hospital Catalogue, pp. 20–21, 23–25, Jun. 1983.
Breastfeeding, A Guide For the Medical Professional, Ruth A. Lawrence, pp. 467–469, l985.

*Primary Examiner*—Sharon Kennedy
*Attorney, Agent, or Firm*—Baniak Nicholas Pine & Gannon

[57] ABSTRACT

A breastpump assembly for either single or double breast-pumping has first and second breastpump units. Each breastpump unit has a breast shield within which a breast is received, and at least one container for collecting breastmilk expressed into a respective breast shield. A pumping mechanism, such as one having a battery power source, generates a periodic reduced pressure within the breast shields, with the pumping unit being carried by the first breastpump unit. A mechanism is advantageously provided for alternating the periodic reduced pressure between the first and second breastpump units.

13 Claims, 7 Drawing Sheets

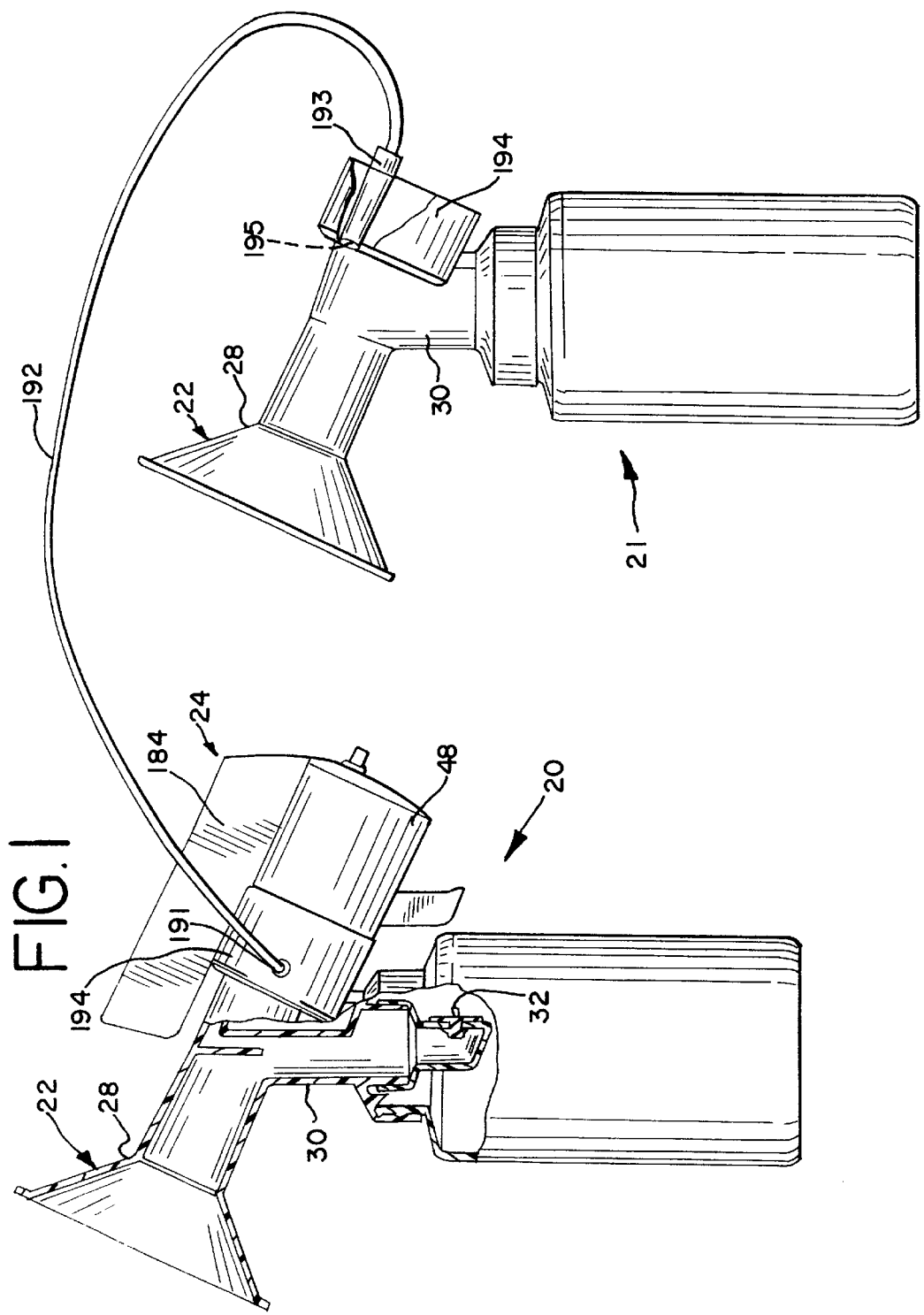

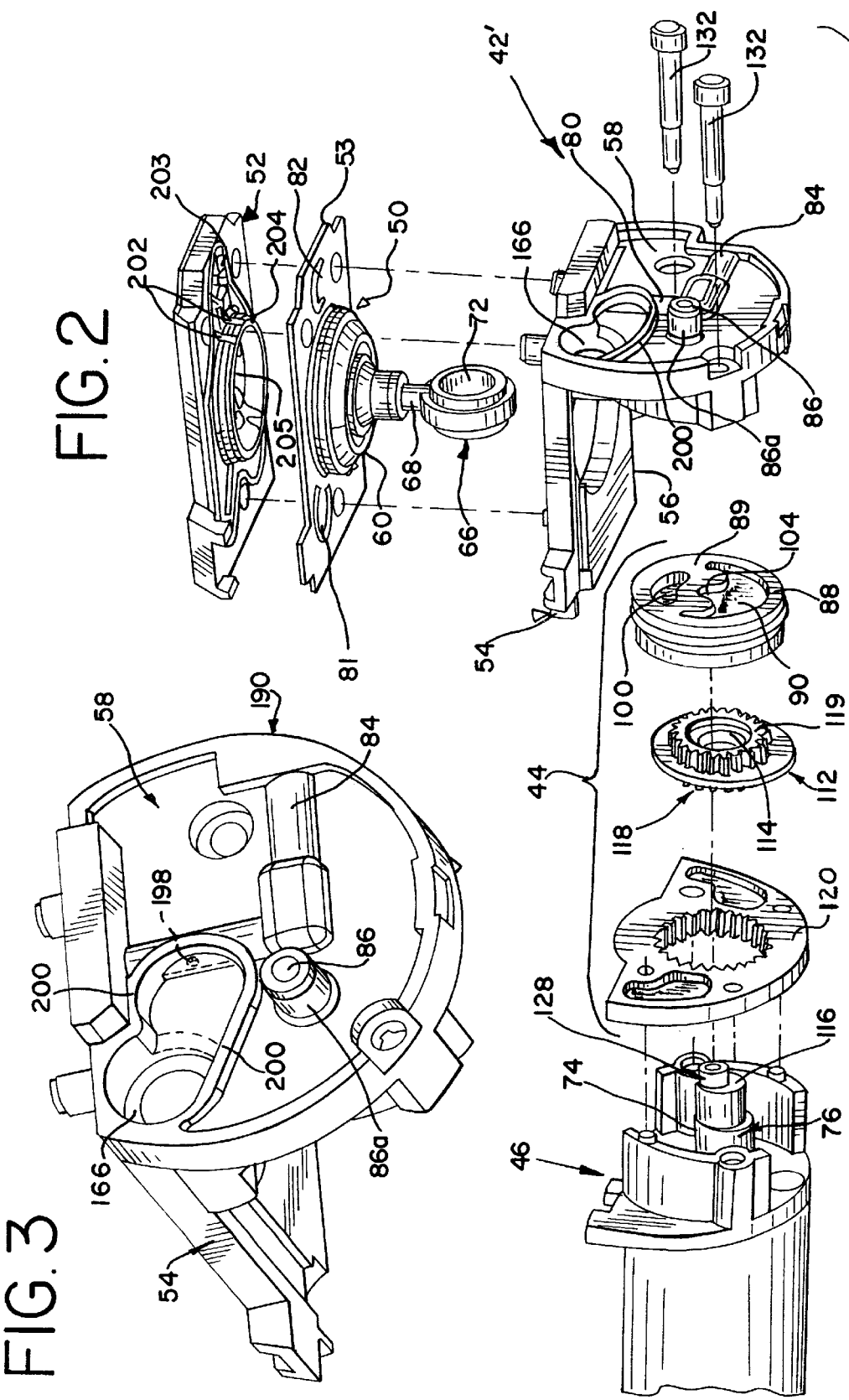

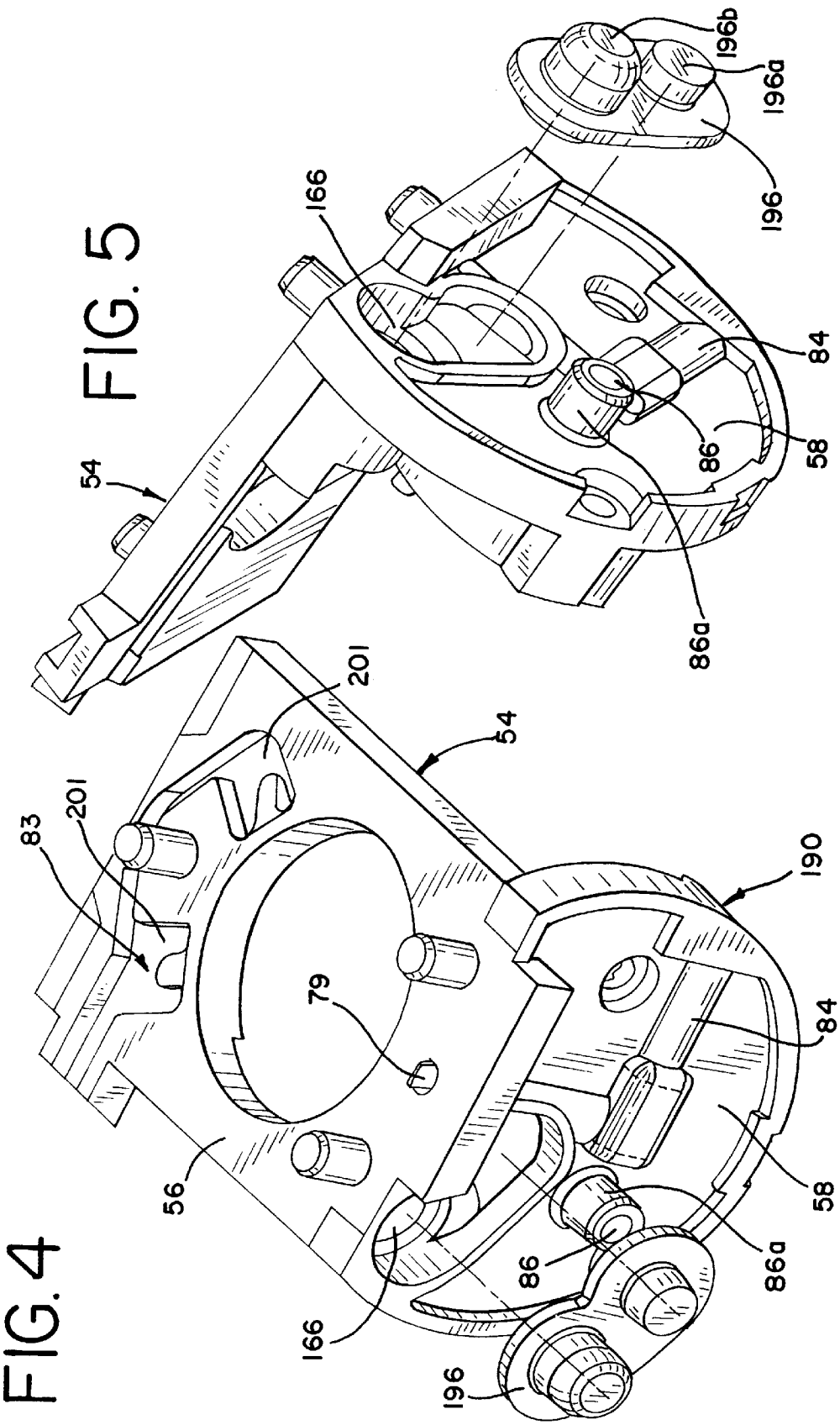

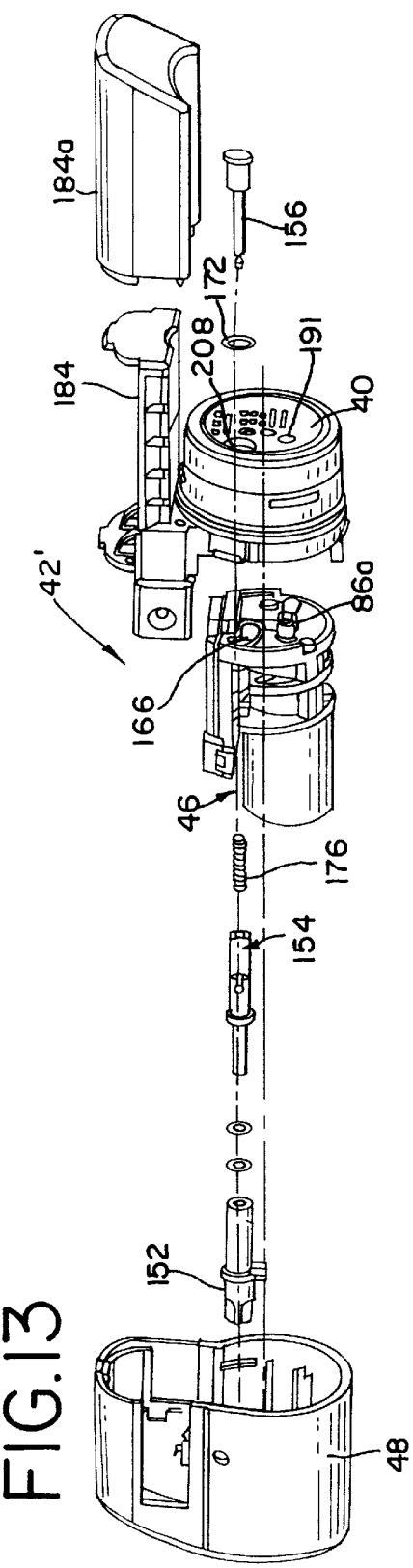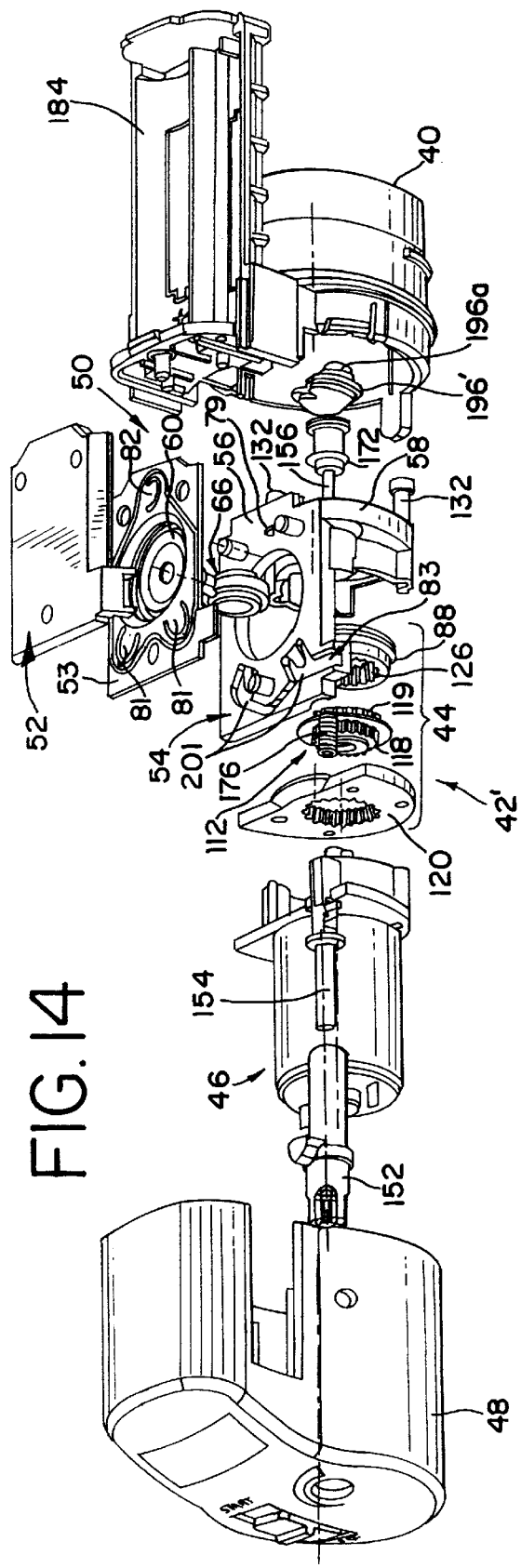

6,139,521

BREASTPUMP HAVING PARTICULAR APPLICATION AS A SMALL MOTORIZED PUMP CAPABLE OF DOUBLE-BREAST PUMPING

This application claims benefit of Provisional Appl. 60/019,085, filed Jun. 3, 1996.

FIELD OF THE INVENTION

This invention relates to breastpumps for drawing breastmilk, and particularly motorized breastpumps.

BACKGROUND OF THE INVENTION

Breastpumps for use by nursing mothers are well known. They allow the nursing woman to express the breastmilk as necessary or convenient, and further provide collection of the breastmilk for later use. For some mothers, breastpumps may be a necessity, such as when the child has suckling problems, or if the mother has problems with excessive or deficient milk production, or soreness, deformation or injury of the mammilla.

Manual breastpumps are commonplace, primarily because they are relatively inexpensive and easy to transport. Being manually driven, however, stroke rate and suction pressure produced can be uneven. Use of a manual pump also may require two hands: one to hold the pump in place, the other to manipulate the piston pump or squeeze-bulb.

Electrically-driven breastpumps are also commonplace. They may be of a substantially large size of a non-portable or semi-portable type, typically including a vacuum pump which has a substantial electric motor that plugs into standard house current. Advantages of this type of pump are ready controllability and regulation of the vacuum, and the ability to pump both breasts at once. That is, the nursing woman has both hands free to hold two breastpump shields in place for pumping of both breasts at the same time.

Battery-driven breastpumps have also been developed. These breastpumps have the advantages of controllability and regulation of the vacuum, as well as being easily carried. Such a battery-driven portable breastpump is described in U.S. Pat. No. 4,964,851, for example. This breastpump, sold under the name MINIELECTRIC by Medela, Inc., is lightweight and achieves good vacuum (i.e., negative pressure) regulation in preferred limits, for example, between 100 and 220 mmHg.

Applicants are not aware, however, of any small hand-held motor-driven breastpump, such as battery-powered, which has been developed for double-breast pumping. Applicants also are not aware of any prior art breastpump which alternates a suction stroke (pull) on two breasts in a double-pumping mode; those breastpumps known to Applicants apply vacuum simultaneously to both of the breasts. It is known, however, to alternate a compression (increased pressure) stroke between two breasts being pumped, but with a continuous vacuum to the breasts, as shown in U.S. Pat. No. 4,607,596.

SUMMARY OF THE INVENTION

The present invention has as a principal objective to provide a breast pump assembly for use in single as well as double breastpumping, comprising first and second breastpump units. In one broad aspect of the invention, the breastpump units are alternately subjected to a suction stroke. In another broad aspect of the invention, the pumping mechanism is of a reduced size, and battery driven, so as to be carried by one of the breastpump units.

The invention more particularly contemplates a motor-powered pump with the motor carried by one of the breastpump units, and which serves both of the breastpump units. In a preferred embodiment, an electrically-driven pumping mechanism for generating a periodic reduced pressure within each breast shield of a respective breastpump unit is carried by the first breastpump unit. An airline from the pumping mechanism connects to the second breast pump unit to convey air pressure changes from the pumping mechanism to the second breastpump unit, while also servicing the first unit.

The preferred double-breastpump assembly includes a pressure distributing mechanism which alternates pressures generated by the pumping mechanism (both negative pressure and return to ambient) between the first and second breastpump units. In this preferred assembly, the pumping mechanism is a diaphragm pump mounted to the first breastpump unit which is powered by at least one battery, also carried by the first breastpump unit.

These and other features and advantages of the present invention will be further understood and appreciated when considered in relation to the following detailed description of an embodiment of the invention taken in conjunction with the drawings, in which:

BRIEF DESCRIPTION OF THE DRAWINGS

FIG. 1 is an elevational view of a breastpump assembly for double-pumping made in accordance with the teachings of this invention;

FIG. 2 is an exploded perspective view of major elements of the pumping mechanism of the breastpump assembly of FIG. 1 in one embodiment;

FIG. 3 is an enlarged perspective view of part of the pumping mechanism of FIG. 2;

FIGS. 4 and 5 are additional and different perspective views of the part of FIG. 3;

FIG. 13 is a perspective view similar to that of FIG. 2, but with the regulator assembly added;

FIG. 14 is another perspective view similar to that of FIGS. 2 and 13;

DETAILED DESCRIPTION OF A PREFERRED EMBODIMENT

Figure 6:
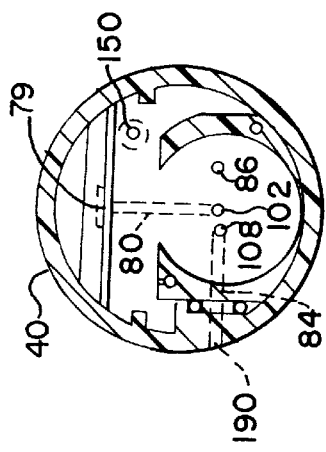
FIG. 6 is a sectional view of the forward end of the pump drive highlighting the inboard side of the membrane deck shown in FIG. 2.

Referring to FIG. 1 initially, a breastpump assembly of the present invention has two breastpumps 20, 21 of the type shown and described in U.S. Pat. No. 4,964,851. Because the present invention is an outgrowth, and improvement upon, the breastpump in the aforementioned '851 patent, the disclosure of the latter patent is incorporated by reference in this application. Certain details in common will therefore be omitted from the present application, since reference to the '851 patent will readily yield the same. Common numbers accordingly refer to the same or substantially the same part in the present application and the '851 patent; numbers bearing a prime (') are similar but modified parts herein.

Each breastpump 20, 21 has a suction bell or shield 22 that is placed on the breast for drawing vacuum within the shield, and thereby drawing milk through a pulling force applied to the breast. The reduced pressure, or vacuum, is generated by a suction drive unit 24 which is shown attached to breastpump 20. Milk drawn from the breast is collected in a collection container 26.

Shield 22 has a forward bell or funnel portion 28 within which the breast is received. A neck or connecting portion 30 extends from the funnel 28 to container 26. Milk drawn into the shield passes through a flap valve 32 of the type shown and described in U.S. Pat. No. 4,929,229.

As set forth in the '851 patent, suction drive unit 24 includes a suction pump assembly 42' (FIGS. 2, 13 and 14), a rotatable valve assembly 44 (FIGS. 2 and 12), and a motor drive 46 for driving the rotatable valve assembly 44 and suction pump assembly 42'. All of the foregoing are contained within a two-piece housing, of which rearward part 48 is shown extending out of a mounting collar 194 in FIG. 1, and forward part 40 is referenced in FIGS. 13 and 14. The forward part 40 is received within the collar 194 and rearward compartment of the breastpump unit 20 in a substantially airtight fit. Motor drive 46 is powered by batteries, which are contained within battery compartment 184 having a cover 184a.

Suction pump assembly 42' has a membrane 50 located between a top plate 52 and a membrane deck 54. It is mounted within a mounting plate 53 (e.g., FIGS. 2, 12 and 14). There is a vertical portion 58 and a horizontal portion 56 to the membrane deck 54 (e.g., FIGS. 3 through 5). With membrane 50 therebetween, a pumping chamber is created in the space between the top plate 52 and a pumping diaphragm portion 60 of the membrane 50.

Details of the top plate 52 are particularly shown in FIGS. 8–11. Essentially, the top plate 52 is designed to sealingly engage with the mounting plate 53 and deck 54 to form the pumping chamber and related air channels. For instance, inlet air channels 202 formed in the top plate 52 extend from a well 203 in communication with flap 82 and passage 80 (FIG. 12), through a ring wall 204 and into an interior dome 205 to the pumping chamber. Outlet air channels 206 extend through the plate collar 204 to flaps 81 and the ports 201 of the outlet channel 83.

Figure 15:
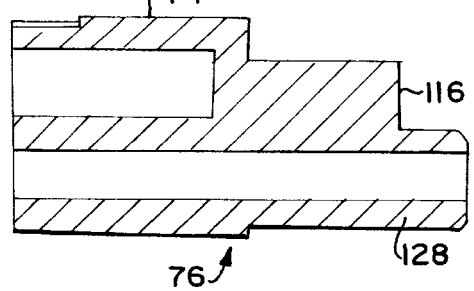
FIG. 15 is an enlarged sectional view of the eccentric cam which is mounted on the motor drive shaft.

Pumping diaphragm portion 60 is reciprocated toward and away from the top plate 52 by a sleeve bearing 66 that includes a driver arm 68. Bearing 66 has an opening 72 that receives an enlarged diameter portion 74 of an eccentrically mounted cam 76 (and see FIG. 15 regarding the cam 76). As the cam 76 is rotated by the drive shaft of the motor 46, portion 74 causes the driver arm 68 (e.g., FIGS. 2 and 12) to move with (in part) a radial motion relative to the cam 76, and thus alternatingly compressing and expanding the volume of the pumping chamber.

On an intake stroke, i.e., expansion of the pumping chamber, air is drawn into the pumping chamber through passage 80 past flap valve 82 and into the pumping chamber via inlet 79 (FIGS. 4, 12 and 14), which is in alternating communication with each shield 22 (via the rotatable valve assembly described hereafter). At the same time that air is being drawn into the pumping chamber, the ports 201 of a channel forming outlet 83 are closed (the opening and closing of the inlet and outlet being obtained by suitable flap valves 82, 81, respectively, again as described in the '851 patent).

On the exhaust or compression stroke of diaphragm portion 60, air drawn into the pumping chamber is forced out through outlet 83, whose flap valves 81 open under this increased pressure. Inlet 79 is in turn closed on this compression stroke.

Figure 18:
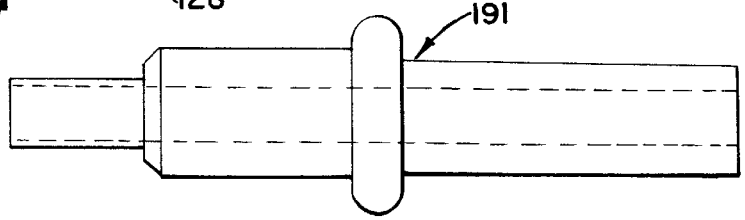
FIG. 18 is an enlarged view of a tubing connector for the pump drive unit.
Figure 17:
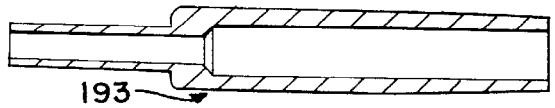
FIG. 17 is an enlarged view of a tubing connector for one breast pump.

The suction generated by the pump assembly 42' is diverted in alternating fashion by the rotatable valve assembly 44 between two passages 84 and 86. Passage 84 communicates with a port 190 to which breastpump 21 is connected via tube 192 using a connector 191 (FIG. 18). The other end of tube 192 fits into a port 195 formed in the mounting collar (such as in the manner shown in U.S. Pat. No. 5,007,899) using a connector 193 (see FIGS. 1 and 17). Passage 86 establishes communication with the shield 22 of breastpump 20 via stud 86a that extends into an opening 191 (FIG. 13) in the forward portion 40 of the housing, which in turn then communicates with the air chamber formed within the mounting collar 194 between the collar, forward portion 40 and the breastpump 20.

The rotatable valve assembly 44 controls the airflow to the breastpumps 20, 21. This assembly 44 has substantially the same elements operating in substantially the same fashion as described in the '851 patent, and reference for specific detail should be made thereto. However, in brief, rotatable disk valve 88 (e.g., FIGS. 2, 12 and 14) has a flat face 89 that abuts against the back of vertical portion 58 in a generally sealing engagement. Passage 80 to the diaphragm pump chamber aligns with central open area 104 of the disk valve 88 at opening 102 (FIG. 6). Arcuate recesses 90 and 100 are caused to place passages 84 and 86 alternately in communication (i.e., opening and closing the passages) with the diaphragm pump chamber and atmosphere in a precisely timed manner as the disk valve 88 rotates and covers and uncovers openings to passages 86 and 84 (the latter passage via opening 108 (FIG. 6)). Negative pressure (vacuum) to the breastpumps 20, 21 is thus alternated in this fashion, as is release of the pressure to atmosphere.

Disk valve 88 is rotated by epicycle gear 112. Disk valve 88 is mounted on a stud-like end 128 of a reduced diameter portion 116 extending from the eccentric cam 76, which end 128 is received within a boss or collar (not shown) on the inboard side of the gear 88. The axis of the stud 128 and the drive shaft of the motor are coincident. Disk valve 88 rotates on this stud 128 via the boss.

Figure 12:
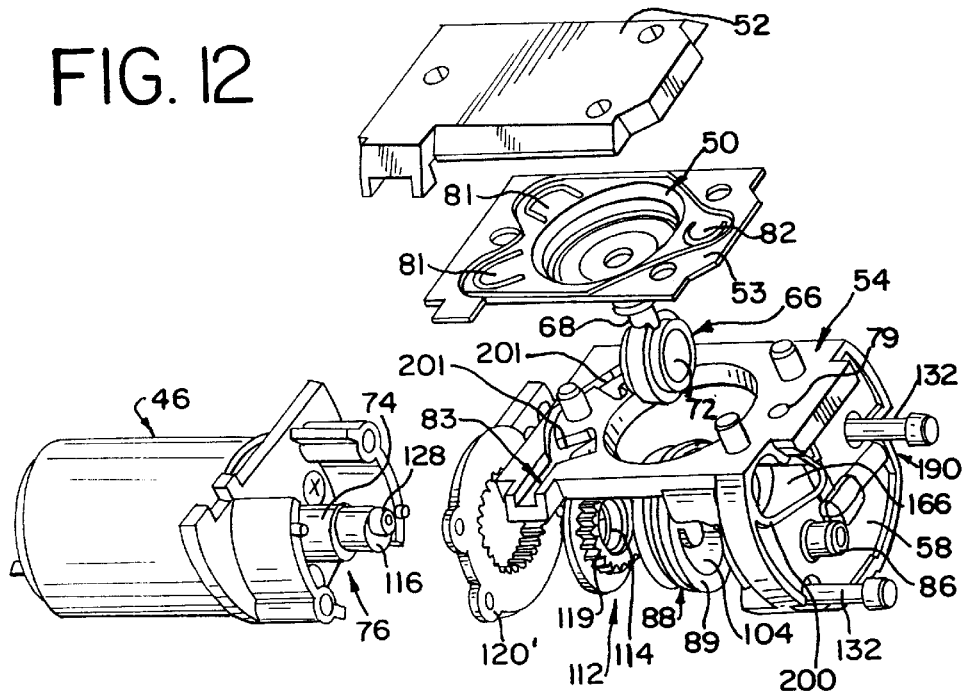
FIG. 12 is another perspective view similar to that of FIG. 2, of a modified embodiment.

Opening 114 in gear 112 receives the eccentrically-mounted reduced diameter portion 116 of cam 76. As seen in FIGS. 2 and 14, gear 112 includes a first gear portion 118 that is in turn received to travel within a stationary gear 120 (FIG. 12 depicts another version of this stationary gear 120'). A second gear portion 119 of gear 112 engages another annular gear 126 (FIG. 14) formed around the inside of disk valve 88. The various gears heretofore described have sizes and ratios designed to achieve the desired cyclic motion for the pump 24 and suction levels, again as more fully described in the '851 patent.

Screws 132 which pass through appropriate apertures in vertical part 58 of the membrane deck 54 and stationary gear 120 and into appropriate mounts of motor 46, are used to fix the disk valve 88 and gears in position, and mount the same to the motor 46.

Figure 7:
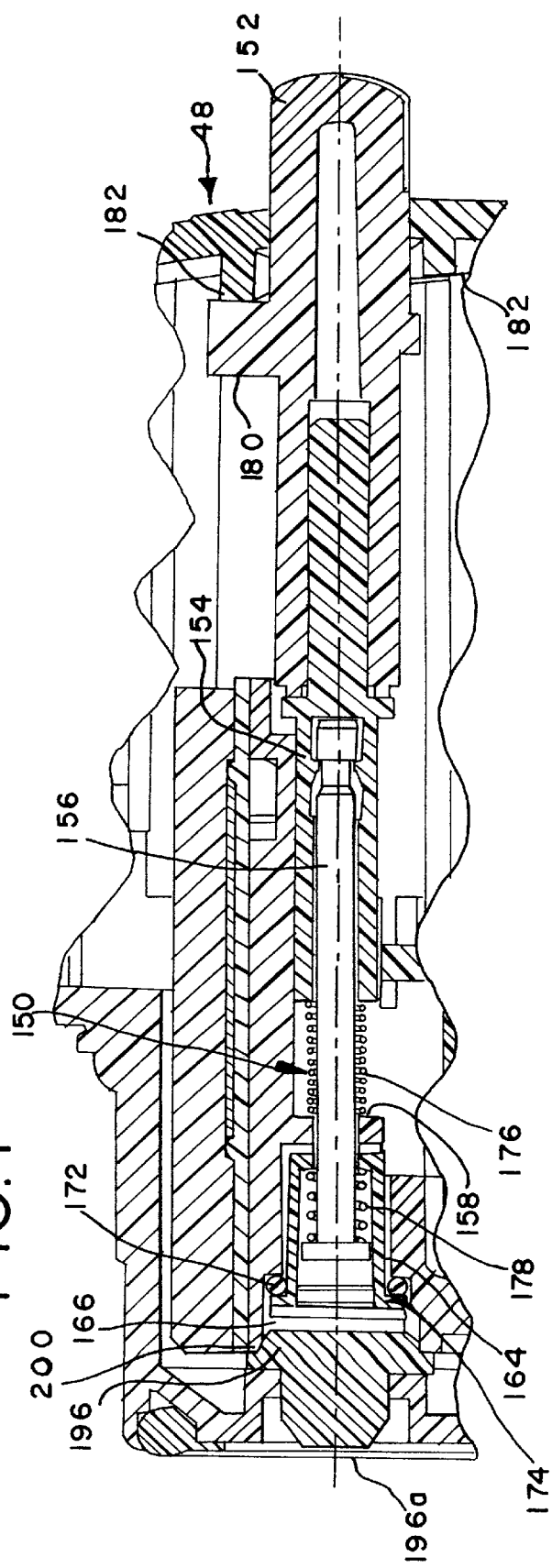
FIG. 7 is an enlarged sectional view showing a pressure regulator assembly.
Figure 8:
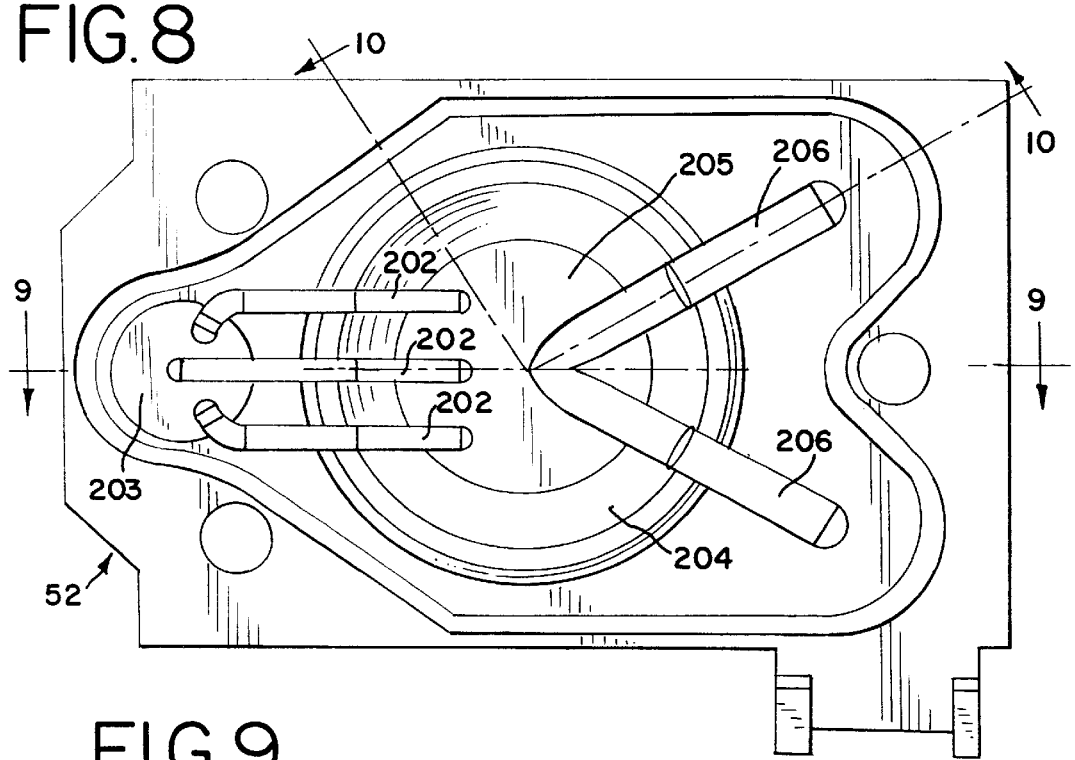
FIG. 8 is an enlarged bottom plan view of the top plate of FIG. 2.
Figure 9:
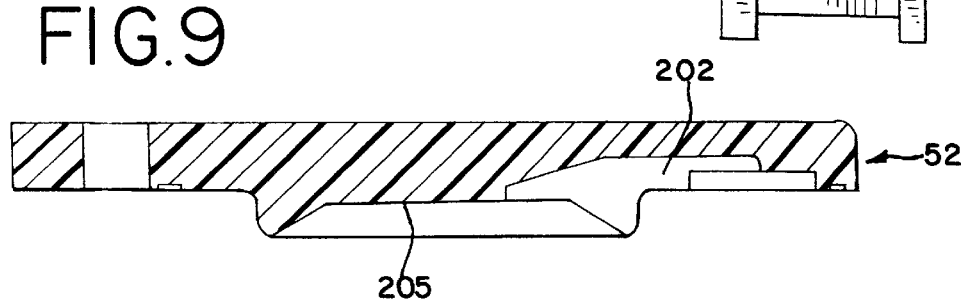
FIG. 9 is a reduced-size sectional view along line 9—9 of FIG. 8.
Figure 10:
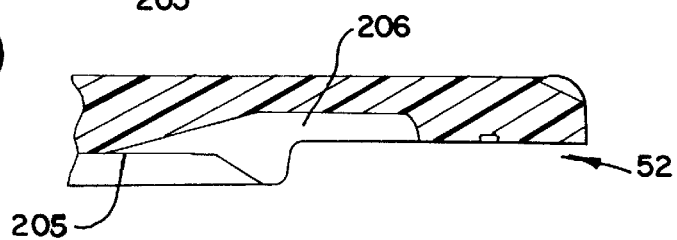
FIG. 10 is a reduced-size sectional view along line 10—10 of FIG. 8.
Figure 11:
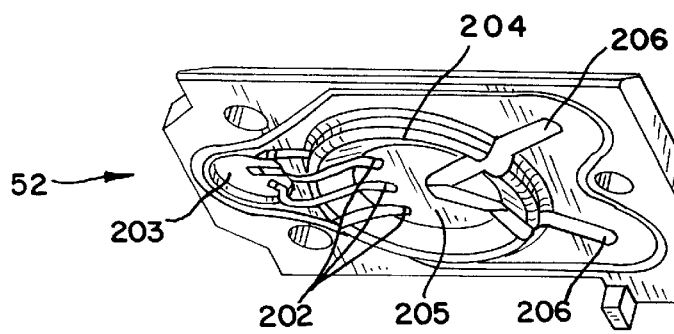
FIG. 11 is a reduced-size bottom perspective view of the top plate of FIG. 8.
Figure 16:
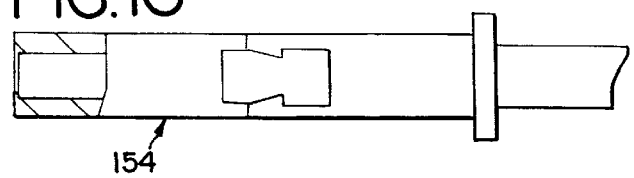
FIG. 16 is an enlarged view, partly in section, of a connector rod used in the regulator assembly.

A regulator valve 150 (FIGS. 7, 13 and 14) is used to adjust the level of suction or negative pressure. It includes an adjustment knob 152 which extends outside of the housing portion 48. Knob 152 engages a plunger 156 via a rod 154 (and see FIG. 16) to which plunger 156 is attached. Plunger 156 extends through an opening 158 (FIG. 7) formed in the membrane deck 54. The forward end of the plunger 156 is received within a cap 164 in a recess 166.

An O-ring seal 172 forms a seal between an annular flange 174 on cap 164 and an internal shoulder of recess 166. The strength of this seal is effected in part by a spring 178 around plunger 156, which serves to bias the enlarged outboard end of the plunger 156 away from the inboard end of the cap 164. As adjustment knob 152 is urged inwardly of housing portion 48, the tension on spring 178 is eased, relaxing the compression of the seal of the O-ring 172. Air in the housing can then be bled past this seal in a controlled manner, which (in contrast to the embodiment described in the '851 patent) is drawn into the pumping chamber on the expansion or suction stroke. The recess 166 is placed within a well defined by wall 200 on the outboard face of the vertical portion 58. An aperture 198 (shown in dotted line fashion in FIG. 3) previously tested with the embodiment of FIG. 2 was eliminated. A silicone plug-like cover 196 (FIGS. 4 and 5) has a kidney-like shape to match that of the wall 200 (e.g., FIG. 12), and has additional bosses 196*a*, 196*b* which are received in apertures, e.g., 208, formed in forward part 40 (FIG. 13). Air from within the housing can thus be metered through the seal in recess 166 and then through hole 198 to adjust the level of vacuum being generated.

In a like manner, when the knob 152 is moved outwardly, the plunger/cap compresses the O-ring further, reducing the amount of air bleed-through. A dog 180 and ramp 182, with the dog biased against ramp 182 by spring 176, are used with knob 152 to effect the longitudinal movement of the plunger 156.

Thus, while an embodiment of the present invention has been described herein, those with skill in this art will recognize changes, modifications, alterations and the like which still shall come within the spirit of the inventive concept, and such are intended to be included within the scope of the invention as expressed in the following claims.

What is claimed is:

1. A double-breastpump assembly for human breastmilk pumping comprising:

first and second breastpump units, each breastpump unit having a breast shield adapted to receive a woman's breast therein;

at least one container for collecting breastmilk expressed into said breast shields, and conduit structure for conveying breastmilk from said breast shields to said container;

an electrically driven pumping mechanism for generating a periodic reduced pressure within said breast shields, said pumping mechanism being carried by said first breastpump unit, with an airline to convey said reduced pressure to said breast shield of said first breastpump unit; and a second airline from said pumping mechanism to said second breastpump unit to convey said reduced pressure to said second breastpump unit.

2. A double-breastpump assembly comprising:

first and second breastpump units, each breastpump unit having a breast shield adapted to receive a woman's breast therein;

at least one container for collecting breastmilk expressed into said breast shields, and conduit structure for conveying breastmilk from said breast shields to said container;

an electrically driven pumping mechanism for generating a periodic reduced pressure within said breast shields, said pumping mechanism being carried by said first breastpump unit, with an airline to convey said reduced pressure to said breast shield of said first breastpump unit;

a second airline from said pumping mechanism to said second breastpump unit to convey said reduced pressure to said second breastpump unit; and a pressure distributing assembly which alternates reduced pressure generated by said pumping mechanism between said first and second breastpump units.

3. A double-breastpump assembly comprising:

first and second breastpump units, each breastpump unit having a breast shield adapted to receive a woman's breast therein;

at least one container for collecting breastmilk expressed into said breast shields, and conduit structure for conveying breastmilk from said breast shields to said container;

an electrically driven pumping mechanism for generating a periodic reduced pressure within said breast shields, said pumping mechanism being carried by said first breastpump unit, with an airline to convey said reduced pressure to said breast shield of said first breastpump unit;

a second airline from said pumping mechanism to said second breastpump unit to convey said reduced pressure to said second breastpump unit; and means for alternating reduced pressure generated by said pumping mechanism between said first and second breastpump units.

4. The double-breastpump assembly of claim 1 wherein said pumping mechanism is a diaphragm pump mounted to said first breastpump unit which is powered by at least one battery also carried by said first breastpump unit.

5. A double-breastpump assembly for human breastmilk pumping, comprising:

first and second breastpump units, each breastpump unit having a funnel-shaped breast shield defining an interior space adapted to receive a woman's breast therein including an extension within which the breast nipple can extend;

at least one container for collecting breastmilk expressed into said breast shields, and conduit structure for conveying breastmilk from said breast shields to said container;

an electrically driven pumping mechanism for generating a periodic reduced pressure within said breast shields, said pumping mechanism including a pumping chamber within which a reduced pressure is generated, first and second outlets from said pumping chamber, and a mechanism for alternatingly connecting said pumping chamber with said first and second outlets, for alternating said periodic reduced pressure between said interior space of said first and second breastpump units; and airline structure connecting said first and second outlets of said pumping mechanism to said shields of said first and second breastpump units to convey air pressure changes from said pumping mechanism to said breastpump units.

6. A double-breastpump assembly comprising:

first and second breastpump units, each breastpump unit having a breast shield adapted to receive a woman's breast therein, a container for collecting breastmilk expressed into a respective breast shield, and conduit structure for conveying breastmilk from said breast shield to its respective container;

a pumping mechanism having a battery power source for generating a periodic reduced pressure within said breast shields, said pumping mechanism and said battery power source being carried by said first breastpump unit and being in air communication with said breast shield of said first breastpump unit to convey said periodic reduced pressure to said breast shield of said first breastpump unit;

an air tube from said pumping mechanism to said second breastpump unit to convey said periodic reduced pressure to said breast shield of said second breastpump unit; and means for alternating said periodic reduced pressure between said breast shields of said first and second breastpump units.

7. A breastpump assembly for human breastmilk pumping comprising:

a first breastpump unit having a funnel-shaped breast shield defining an interior space adapted to receive a woman's breast therein;

a container for collecting breastmilk expressed into said breast shield, and milk conduit structure for conveying breastmilk from said breast shield to said container;

a source of vacuum for generating reduced air pressure within said breast shield;

a manifold having first and second outlets, and vacuum conduit structure for conveying said vacuum to said manifold; and a distributor mechanism for cyclically and alternatingly connecting vacuum in said manifold to said outlets, with said first breastpump interior space having an air line which communicates with said first outlet.

8. The breastpump assembly of claim 7 further including a second breastpump unit, said second breastpump unit having a breast shield and an interior space adapted to receive a woman's breast therein with a second air line which communicates with said second outlet for double breast pumping.

9. The breastpump assembly of claim 8 further including a pumping mechanism which is a motor driven diaphragm pump mounted to and carried by said first breastpump unit, and said second air line is a tube connecting said second outlet with said breast shield of said second breastpump unit.

10. A breast pump assembly for single as well as double-breastpumping of a woman comprising:

first and second breastpump units, each breastpump unit having a breast shield adapted to receive a woman's breast therein;

at least one container for collecting breastmilk expressed into said breast shields, and conduit structure for conveying breastmilk from said breast shields to said container;

a motor-driven pumping mechanism for generating a periodic reduced pressure within said breast shields, said pumping mechanism being carried by said first breastpump unit, and having two outlets for said reduced pressure;

an airline to convey said reduced pressure from one of said outlets to said breast shield of said first breastpump;

a second airline connectable to the other of said outlets of said pumping mechanism to said second breastpump unit to convey said reduced pressure air from said pumping mechanism to said second breastpump unit;

whereby said breastpump assembly can be used in a single as well as double breastpumping mode of operation by connecting said second breastpump unit to said pumping mechanism via said second airline.

11. The breastpump assembly of claim 10 wherein said pumping mechanism is a diaphragm pump mounted to said first breastpump unit which is powered by at least one battery also carried by said first breastpump unit.

12. A breast pump assembly for single as well as double-breastpumping comprising:

first and second breastpump units, each breastpump unit having a breast shield adapted to receive a woman's breast therein;

at least one container for collecting breastmilk expressed into said breast shields, and conduit structure for conveying breastmilk from said breast shields to said container;

a motor-driven pumping mechanism for generating a periodic reduced pressure within said breast shields, said pumping mechanism being carried by said first breastpump unit, and having two outlets for said reduced pressure;

an airline to convey said reduced pressure from one of said outlets to said breast shield of said first breastpump;

a second airline connectable to the other of said outlets of said pumping mechanism to said second breastpump unit to convey said reduced pressure air from said pumping mechanism to said second breastpump unit; and a pressure distributing assembly which cyclically alternates pressures generated by said pumping mechanism between said first and second breastpump units whereby said breastpump assembly can be used in a single as well as double breastpumping mode of operation by connecting said second breastpump unit to said pumping mechanism via said second airline.

13. The breastpump of claim 11 wherein said distributing assembly includes a manifold through which said reduced pressure flows which is in communication with said two outlets, and a distributor mechanism for cyclically and alternatingly connecting said reduced pressure in said manifold to said outlets.

* * * * *